United States Patent [19]

Rayudu

[11] Patent Number: 4,650,866
[45] Date of Patent: Mar. 17, 1987

[54] PROCESS OF PREPARING 1-METHYL-3,5,7-TRIAZA-1-AZONIATRICYCLODECANE HALIDES

[75] Inventor: S. Rao Rayudu, Germantown, Tenn.

[73] Assignee: Buckman Laboratories, Inc., Memphis, Tenn.

[21] Appl. No.: 837,039

[22] Filed: Mar. 6, 1986

[51] Int. Cl.$^4$ ............................................ C07D 487/18
[52] U.S. Cl. ..................................................... 544/186
[58] Field of Search ......................................... 544/186

[56] References Cited

PUBLICATIONS

Friedrich et al, Berichte, vol. 54B, pp. 1531–1542 (1921).
Friedrich et al, Chem. Abstracts, vol. 15, pp. 3615–3616 (1921).

Primary Examiner—John M. Ford
Attorney, Agent, or Firm—Finnegan, Henderson, Farabow, Garrett & Dunner

[57] ABSTRACT

A process for preparing 1-methyl-3,5,7-triaza-1-azoniatricyclodeane halides. Ammonium halide, methylamine, formaldehyde and ammonia are reacted in an aqueous system.

19 Claims, No Drawings

PROCESS OF PREPARING 1-METHYL-3,5,7-TRIAZA-1-AZONIATRICYCLO-DECANE HALIDES

BACKGROUND OF THE INVENTION

This invention relates to the preparation of organic compounds and more particularly to the preparation of quaternary ammonium salts of hexamethylenetetramine which are useful as microbicides.

These organic quaternary ammonium salts are more specifically designated as 1-methyl-3,5,7-triaza-1-azoniatricyclodecane fluoride, chloride, bromide, and iodide which have the formula (I)

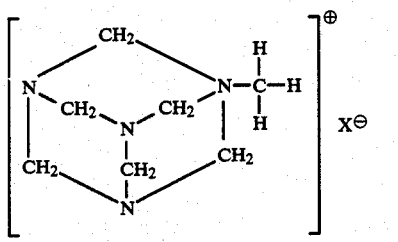

wherein X is fluoride, chloride, bromide, or iodide.

Friedrich et al. (Ber. 54B, 1531-42, 1921) have reported the preparation of such compounds, specifically 1-methyl-3,5,7-triaza-1-azoniatricyclodecane chloride, by refluxing a mixture of formaldehyde, ammonium hydroxide and ammonium chloride for 7 hours. As shown in Comparative Example 1, the reaction time for this reaction is unusually long and the yields of the desired product are disadvantageously low.

It is, therefore, a principal object of the present invention to obviate the disadvantages of the prior art processes and to provide an improved process for the preparation of the quarternary ammonium compounds of formula (I).

It is another object of the invention to provide an economical process for the preparation of these compounds as aqueous solutions.

These and other objects and advantages will become apparent as the description proceeds.

SUMMARY OF THE INVENTION

The present invention is a process of preparing a compound of the formula (I):

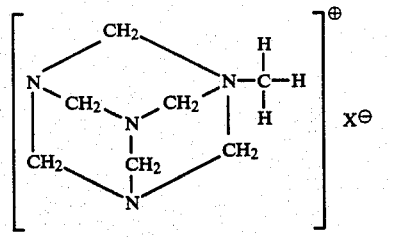

wherein X is a halide anion selected from the group consisting of fluoride, chloride, bromide, and iodide, which comprises the step of reacting ammonium halide with methylamine, formaldehyde, and ammonia in an aqueous medium for a time sufficient to prepare the compound of formula (I). Preferably, an aqueous reaction medium of ammonium halide, methylamine, and formaldehyde is prepared, followed by addition of sufficient ammonia to bring the pH of the final reaction medium within the range of about 6 to 8.

DETAILED DESCRIPTION OF THE PREFERRED EMBODIMENTS

The quaternary ammonium salts of formula (I) are prepared in accordance with the present invention by reacting an ammonium halide, preferably ammonium chloride, ammonium bromide, or ammonium iodide, with methylamine, formaldehyde, and ammonia in an aqueous system. All of these starting materials for the process of the present invention are readily available commercial products.

In the reaction of the present invention, each mole of ammonium halide is preferably reacted with about 0.75 to 1.25 moles of methylamine as a source of an N-methyl group, 5.75 to 6.25 moles of formaldehyde, and 1.75, more preferably 2, or more moles, of ammonia. Most preferably, from 2 to 2.4 moles of ammonia per mole of ammonium halide are used in the reaction.

The process of the present invention is preferably conducted at a temperature of from about 40° to 70° C. More preferably, the process is conducted in the range of about 45° to 50° C.

The process of the present invention is preferably run by forming an aqueous reaction medium by treating formaldehyde with a mixture of ammonium halide and methylamine while keeping the temperature around about 45° C.

Ammonia is then preferably added to the reaction medium, the temperature of which is preferably kept below 50° C. The amount of ammonia added is preferably 1.75, more preferably 2, or more moles per mole of ammonium halide to bring the pH of the final reaction medium, preferably an aqueous solution, within the range of from about 6 to 8.

The reaction is conducted for a time sufficient to prepare the quaternary ammonium salt of formula (I). Preferably, the reaction is conducted for about 2 hours to 6 hours, more preferably for about 2 hours.

The following examples illustrate the invention, but do not serve as limitations thereon.

COMPARATIVE EXAMPLE 1

Preparation of 1-methyl-3,5,7-triaza-1-azoniatricyclodecane chloride

A 250 ml, three-neck round-bottom flask equipped with a reflux condenser, a mechanical stirrer, and a thermometer was charged with 22 g (0.410 moles) of ammonium chloride and 129 g (1.59 moles) of 37% aqueous formaldehyde. To the above well-agitated mixture were added 40 g (0.286 moles) of 25% aqueous ammonium hydroxide. After completing the addition of ammonium hydroxide, the solution was heated at reflux for 7 hours. The resulting water-clear solution was analyzed by HPLC. The solution contained 5.6% (24.7% yield) by weight of the 1-methyl-3,5,7-triaza-1-azoniatricyclodecane chloride.

EXAMPLE 2

Preparation of 1-methyl-3,5,7-triaza-1-azoniatricyclodecane chloride

A 2.0 liter, three-neck flask equipped with a reflux condenser, a mechanical stirrer, a thermometer and a dropping funnel was charged with 67.0 g (1.25 moles) of ammonium chloride, and 78.0 g (1.25 moles) of 50% aqueous methylamine. To the above well-agitated mixture were slowly added 608.0 g (7.5 moles) of 37% aqueous formaldehyde, while maintaining the temperature between 45° and 50° C. After completing this addition and while continuing vigorous agitation, 175.0 g (3 moles) of 29% aqueous ammonia were introduced at such a rate as to maintain the temperature between 45° and 50° C. Stirring was continued for an additional 2 hours while the temperature fell gradually to the ambient. The resulting water-clear solution was analyzed by HPLC. This solution contained 23% (89% yield) by weight of the 1-methyl-3,5,7-triaza-1-azoniatricyclodecane chloride.

EXAMPLE 3

Preparation of 1-methyl-3,5,7-triaza-1-azoniatricyclodecane bromide

A 2.0 liter, three-neck flask equipped with a reflux condenser, a mechanical stirrer, a thermometer and a dropping funnel was charged with 98.0 g (1.25 moles) of ammonium bromide, and 78.0 g (1.25 moles) of 50% aqueous methylamine. To the above well-agitated mixture were slowly added 608.0 g (7.5 moles) of 37% aqueous formaldehyde, while maintaining the temperature between 45° and 50° C. After completing the addition and while continuing vigorous agitation, 175.0 g (3 moles) of 29% aqueous ammonia were introduced at such a rate as to maintain the temperature between 45° and 50° C. Stirring was continued for an additional 2 hours while the temperature fell gradually to the ambient. The resulting water-clear solution was analyzed by HPLC. The solution contained 24.7% (83% yield) by weight of the 1-methyl-3,5,7-triaza-1-azoniatricyclodecane bromide.

EXAMPLE 4

Preparation of 1-methyl-3,5,7-triaza-azoniatricyclodecane iodide

A 250 ml, three-neck round-bottom flask equipped with a reflux condenser, a mechanical stirrer, a thermometer, and a dropping funnel was charged with 36.3 g (0.250 moles) of ammonium iodide, and 15.6 g (0.250 moles) of 50% aqueous methylamine. To the above well-agitated mixture were slowly added 121.6 g (1.5 moles) of 37% aqueous formaldehyde, while maintaining the temperature between 45° and 50° C. After completing the addition and while continuing vigorous agitation, 30.4 g (0.500 moles) of 29% aqueous ammonia were introduced at such a rate as to maintain the temperaure between 45° and 50° C. Stirring was continued for an additional 2 hours, while the temperature fell gradually to the ambient. The resulting water-clear solution was analyzed by HPLC. The solution contained 29.0% (86% yield) by weight of the 1-methyl-3,5,7-triaza-1-azoniatricyclodecane iodide.

While particular embodiments of the invention have been described, it will be understood, of course, that the invention is not limited thereto since many modifications may be made, and it is, therefore, contemplated to cover by the appended claims any such modifications as fall within the true spirit and scope of the invention.

What is claimed is:

1. A process of preparing a compound of the formula (I):

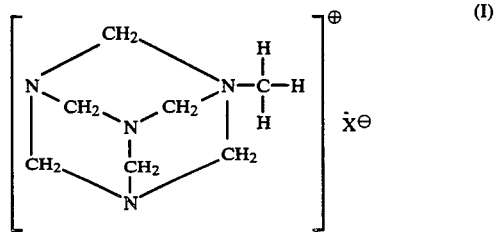

wherein X is a halide anion selected from the group consisting of fluoride, chloride, bromide, and iodide, which comprises the step of reacting ammonium halide with methylamine, formaldehyde, and ammonia in an aqueous medium for a time sufficient to prepare said compound of formula (I).

2. The process of claim 1, wherein each mole of ammonium halide is reacted with 0.75 to 1.25 moles of methylamine, 5.75 to 6.25 moles of formaldehyde, and 1.75 or more moles of ammonia.

3. The process of claim 2, wherein each mole of ammonium halide is reacted with 2 to 2.4 moles of ammonia.

4. The process of claim 1, wherein the temperature is maintained at about 45°-50° C.

5. The process of claim 1, wherein the reaction is conducted for from about two to six hours.

6. The process of claim 1, wherein X is chloride.

7. The process of claim 6, wherein each mole of ammonium chloride is reacted with 0.75 to 1.25 moles of methylamine, 5.75 to 6.25 moles of formaldehyde, and 1.75 or more moles of ammonia, wherein the temperature is maintained at about 45°-50° C., and wherein the reaction is conducted for from about two to six hours.

8. The process of claim 1, wherein X is bromide.

9. The process of claim 8, wherein each mole of ammonium bromide is reacted with 0.75 to 1.25 moles of methylamine, 5.75 to 6.25 moles of formaldehyde, and 1.75 or more moles of ammonia, wherein the temperature is maintained at about 45°-50° C., and wherein the reaction is conducted for from about two to six hours.

10. The process of claim 1, wherein X is iodide.

11. The process of claim 10, wherein each mole of ammonium iodide is reacted with 0.75 to 1.25 moles of methylamine, 5.75 to 6.25 moles of formaldehyde, and 1.75 or more moles of ammonia, wherein the temperature is maintained at about 45°-50° C., and wherein the reaction is conducted for from about two to six hours.

12. The process of claim 1, wherein the reaction is conducted by forming an aqueous reaction medium of said ammonium halide, methylamine and formaldehyde, followed by adding said ammonia to said reaction medium in an amount sufficient to adjust the pH of said reaction medium to from about 6 to 8.

13. The process of claim 12, wherein said reaction medium containing said ammonia is an aqueous solution.

14. The process of claim 13, wherein X is chloride.

15. The process of claim 14, wherein each mole of ammonium chloride is reacted with 0.75 to 1.25 moles of methylamine, 5.75 to 6.25 moles of formaldehyde, and 1.75 or more moles of ammonia, wherein the temperature is maintained at about 45°-50° C., and wherein the reaction is conducted for from about two to six hours.

16. The process of claim 13, wherein X is bromide.

17. The process of claim 16, wherein each mole of ammonium bromide is reacted with 0.75 to 1.25 moles of methylamine, 5.75 to 6.25 moles of formaldehyde, and 1.75 or more moles of ammonia, wherein the temperature is maintained at about 45°–50° C., and wherein the reaction is conducted for from about two to six hours.

18. The process of claim 13, wherein X is iodide.

19. The process of claim 18, wherein each mole of ammonium iodide is reacted with 0.75 to 1.25 moles of methylamine, 5.75 to 6.25 moles of formaldehyde, and 1.75 or more moles of ammonia, wherein the temperature is maintained at about 45°–50° C., and wherein the reaction is conducted for from about two to six hours.

* * * * *